United States Patent
Spibey

(10) Patent No.: US 9,234,182 B2
(45) Date of Patent: Jan. 12, 2016

(54) RECOMBINANT ATTENUATED PARVOVIRUS

(75) Inventor: Norman Spibey, Milton Keynes (GB)

(73) Assignee: Intervet Inc., Madison, NJ (US)

( * ) Notice: Subject to any disclaimer, the term of this patent is extended or adjusted under 35 U.S.C. 154(b) by 252 days.

(21) Appl. No.: 13/581,917

(22) PCT Filed: Mar. 3, 2011

(86) PCT No.: PCT/EP2011/053164
§ 371 (c)(1),
(2), (4) Date: Aug. 30, 2012

(87) PCT Pub. No.: WO2011/107534
PCT Pub. Date: Sep. 9, 2011

(65) Prior Publication Data
US 2012/0328652 A1    Dec. 27, 2012

Related U.S. Application Data

(60) Provisional application No. 61/311,032, filed on Mar. 5, 2010.

(30) Foreign Application Priority Data

Mar. 5, 2010 (EP) .................................. 10155646

(51) Int. Cl.
| | | |
|---|---|---|
| C12N 7/00 | (2006.01) | |
| A61K 39/23 | (2006.01) | |
| A61K 39/12 | (2006.01) | |
| A61K 39/00 | (2006.01) | |

(52) U.S. Cl.
CPC . *C12N 7/00* (2013.01); *A61K 39/12* (2013.01); *A61K 39/23* (2013.01); *A61K 2039/5254* (2013.01); *A61K 2039/5256* (2013.01); *A61K 2039/552* (2013.01); *C12N 2750/14334* (2013.01); *C12N 2750/14362* (2013.01)

(58) Field of Classification Search
CPC ........... C12N 2750/14334; C12N 2770/24134; C12N 2760/18434; C12N 2760/18734; C12N 2760/20234; C12N 2770/10034; C12N 2710/10034; C12N 2710/10334; C12N 2710/16721
See application file for complete search history.

(56) References Cited

FOREIGN PATENT DOCUMENTS

| WO | 00/28004 A1 | 5/2000 |
|---|---|---|
| WO | 2008/157236 A1 | 12/2008 |

OTHER PUBLICATIONS

Cavalli et al., "Evaluation of the Antigenic Relationships among Canine Parvovirus Type 2 Variants", Clinical and Vaccine Immunology, 2008, pp. 534-539, vol. 15, No. 3.
European Search Report for EP 10 15 5646 dated Aug. 27, 2010.
(Continued)

*Primary Examiner* — Michelle S Horning

(57) ABSTRACT

The invention is in the field of virus vaccines for protecting animals against infection by parvovirus, their production and use. More in particular, the invention is related to a vaccine comprising an attenuated parvovirus comprising a capsid protein or fragment thereof derivable from another parvovirus. Surprisingly it was found that such a vaccine was capable of inducing higher titers of protecting antibodies against a challenge with the second type of parvovirus strains while maintaining good immunity against the first type of parvovirus. Recombinant virus strains also remained attenuated.

**16 Cla

(56) References Cited

OTHER PUBLICATIONS

Figure 1:
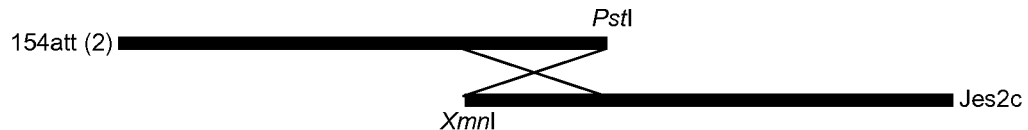

Appel et al., "Isolation and immunisation studies of a canine parvo-like virus from dogs with haemorrhagic enteritis", The Veterinary Record, 1979, pp. 156-159, vol. 105.

Buonavoglia et al., "Evidence for evolution of canine parvovirus type 2 in Italy", Journal of General Virology, 2001, pp. 3021-3025, vol. 82.

Chinchkar et al., "Analysis of VP2 gene sequences of canine parvovirus isolates in India", Archives of Virology, 2006, pp. 1881-1887, vol. 151.

Decaro et al., "First Detection of Canine Parvovirus Type 2c in Pups with Haemorrhagic Enterities in Spain", J. Vet Med. B, 2006, pp. 468-472, vol. 53.

Greenwood et al., "Comparison of isolates of canine parvovirus by restriction enzyme analysis, and vaccine efficacy against field strains", 1995, pp. 63-67, vol. 136.

Kelly, W. R., "An Enteric Disease of Dogs Resembling Feline Panleucopaenia", Australian Veterinary Journal, 1978, p. 593, vol. 54.

Martella et al., "Evolution of CPV-2 and implicance for antigenic/genetic characterization", Virus Genes, 2006, pp. 11-13, vol. 33.

Martella et al., "A Canine Parvovirus Mutant Is Spreading in Italy", Journal of Clinical Microbiology, 2004, p. 1333-1336, vol. 42, No. 3.

Mochizuki et al., "Recombination Between Vaccine and Field Strains of Canine Parvovirus is Revealed by Isolation of Virus in Canine and Feline Cell Cultures", J. Vet. Med. Sci., 2008, pp. 1305-1314, vol. 70, No. 12.

Nakamura et al., "A novel antigenic variant of Canine parvovirus from a Vietnamese dog", Archives of Virology, 2004, pp. 2261-2269, vol. 149.

Parrish et al., "Natural Variation of Canine Parvovirus", Science, 1985, pp. 1046-1048, vol. 230.

Parrish et al., Rapid Antigenic-Type Replacement and DNA Sequence Evolution of Canine Parvovirus, Journal of Virology, 1991, pp. 6544-6552, vol. 65, No. 12.

Parrish et al., "Characterization and Recombination Mapping of an Antigenic and Host Range Mutation of Canine Parvovirus", Virology, 1986, pp. 121-132, vol. 148.

Pereira et al., "Selective regimen shift and demographic growth increase associated with emergence of high-fitness variants of canine parvovirus", Infection, Genetics and Evolution, 2007, pp. 399-409, vol. 7.

Pratelli et al., "Canine Parvovirus (CPV) Vaccination: Comparison of Neutralizing Antibody Responses in Pups after Inoculation with CPV2 or CPV2b Modified Live Virus Vaccine", Clincial and Diagnostic Laboratory Immunology, 2001, pp. 612-615, vol. 8, No. 3.

Shien et al., "Identification of sequence changes in live attenuated goose parvovirus vaccine strains developed in Asia and Europe", Avian Pathology, 2008, pp. 499-505, vol. 37, No. 5.

Spibey et al., "Canine parvovirus type 2 vaccine protects against virulent challenge with type 2c virus", Veterinary Microbiology, 2008, pp. 48-55, vol. 128.

Strassheim et al., "Two Dominant Neutralizing Antigenic Determinants of Canine Parvovirus Are Found on the Threefold Spike of the Virus Capsid", Virology, 1994, pp. 175-184, vol. 198.

Truyen et al., "Evolution of Canine Parvovirus Involved Loss and Gain of Feline Host Range", Virology, 1996, pp. 186-189, vol. 215.

Truyen et al., "Evolution of the Feline-Subgroup Parvoviruses and the Control of Canine Host Range in Vivo", Journal of Virology, 1995, pp. 4702-4710, vol. 69, No. 8.

Truyen, U., "Emergence and recent evolution of canine parvovirus", Veterinary Microbiology, 1999, pp. 47-50, vol. 69.

Wang et al., "Phylogenetic Analysis of Canine Parvovirus VP2 Gene in Taiwan", Virus Genes, 2005, pp. 171-174, vol. 31, No. 2.

International Search Report for corresponding Application No. PCT/EP2011/053164, mailed on Apr. 8, 2011.

RECOMBINANT ATTENUATED PARVOVIRUS

CROSS-REFERENCE TO RELATED APPLICATIONS

This application is a national stage entry under 35 U.S.C. §371 of PCT/EP2011/053164, filed on Mar. 3, 2011, which claims priority to U.S. Provisional Application No. 61/311,032, filed on Mar. 5, 2010, and EP Application No. 10155646.2, filed on Mar. 5, 2010. The content of PCT/EP2011/053164 is hereby incorporated by reference in its entirety.

FIELD OF THE INVENTION

The invention is in the field of virus vaccines for protecting animals against infection by parvovirus, their production and use. More in particular, the invention is related to a vaccine comprising an attenuated parvovirus comprising a capsid protein or fragment thereof derivable from a new parvovirus isolate.

BACKGROUND OF THE INVENTION

Parvovirus belongs to the family of single stranded DNA viruses. Parvoviruses can cause disease in some animals like cats, dogs and pigs. Because the viruses require actively dividing cells in order to replicate, the type of tissue infected varies with the age of the animal. The gastrointestinal tract and lymphatic system can be affected at any age, leading to vomiting, diarrhea and immunosuppression, but cerebellar hypoplasia is only seen in cats that were infected in the womb or at less than two weeks of age, and disease of the myocardium is seen in puppies infected between the ages of three and eight weeks.

Canine parvovirus is a particularly deadly disease among young puppies, about 80% fatal, causing gastrointestinal tract damage and dehydration as well as a cardiac syndrome in very young pups. It is spread by contact with an infected dog's feces. Symptoms include lethargy, severe diarrhea, fever, vomiting, loss of appetite, and dehydration. Porcine parvovirus causes a reproductive disease in swine known as SMEDI, which stands for stillbirth, mummification, embryonic death, and infertility. Feline panleukopenia is common in kittens and causes fever, low white blood cell count, diarrhea, and death. Infection of the cat fetus and kittens less than two weeks old causes cerebellar hypoplasia. Mink enteritis virus is similar in effect to feline panleukopenia, except that it does not cause cerebellar hypoplasia. A different parvovirus causes Aleutian Disease in minks and other mustelids, characterized by lymphadenopathy, splenomegaly, glomerulonephritis, anemia, and death. The most accurate diagnosis of parvovirus is by ELISA. Dogs, cats and swine can be vaccinated against parvovirus.

At the DNA level, canine, feline and porcine parvoviruses are known to have a highly homologous genome. Canine parvovirus (CPV2) is a virus which is responsible for an acute and sometimes fatal enteritis in dogs (Kelly, Aust. Vet. J. 54; 593, 1978; Appel et al., Vet. Rec. 105; 156-159, 1979). The virus, which first appeared around 1977, probably arose from a very closely related virus in cats, feline panleukopaenia virus (FPLV) through a small number of mutations in the single capsid protein; a species jump which may have involved intermediate passage in other carnivores such as mink or raccoons (Truyen et al., Virology 215, 186-189, 1996).

As early as 1979 the first variants of CPV2 appeared, termed CPV2a, and they were quickly followed by the appearance of CPV2b in 1984. (Parrish et al., Science 230, 1046-1048, 1985, and J. Virol. 65; 6544-6552, 1991).

The original type 2 virus has now disappeared from the field having been replaced by the 2a and 2b variants; although the relative proportions of these two types varies from country to country (Truyen et al., supra; Chinchkar et al., Arch. Virol. 151, 1881-1887, 2006; Pereira et al., Infect. Genet. Evol. 3, 399-409, 2007). The amino acid changes in the capsid protein (VP2), which characterise the shift from 2 to 2a and to 2b, are very limited. Substitutions at positions 87 (Met to Leu), 300 (Gly to Ala), 305 (Tyr to Asp) and 555 (Val to Ile) occurred in the evolution of 2 to 2a and 426 (Asn to Asp) and 555 (Ile to Val) in the emergence of 2b from 2a (Parrish et al., supra; Truyen et al., J. Virol. 69, 4702-4710, 1995). Recently, 2a strains lacking the Val to Ile substitution at position 555 have been reported (Wang et al., Virus Genes 31, 171-174, 2005; Martella et al., Virus Genes 33, 11-13, 2006). It appeared that a single amino acid change can differentiate the CPV2a and CPV2b VP2 sequences.

More recently strains have emerged in Italy in which the amino acid at position 426 (Asn in 2a and Asp in 2b) has become a glutamic acid (Glu) residue (Buonavoglia et al., J. Gen. Virol. 82, 3021-3025, 2001; Martella et al., J. Clin. Microbiol. 42, 1333-1336, 2004). The fact that these Glu 426 variants, termed CPV2c viruses, are circulating and co-existing with other CPV types in Italy and other European countries (Decaro et al., J. Vet. Med. B. Infect. Dis. Vet. Public Health 53, 468-472, 2006) and have also been isolated in countries as geographically diverse as Vietnam and Scotland (Nakamura et al., Arch Virol.149, 2261-2269, 2004, Spibey et al., Vet. Microbiol 128, 48-55, 2008) suggests that they have an advantage in at least a proportion of the dog population.

The relatively rapid evolution of canine parvovirus has resulted in the loss and then re-gaining of the feline host range (Truyen et al., 1996 supra), and this regained ability to replicate in cats may well account for the replacement of the original type 2 virus with the 2a, 2b and 2c variants. In the late 1970s and early 1980s both live and inactivated FPL vaccines were used to protect dogs against CPV disease due to the shared antigens which stimulated cross-protection, however the levels of protection they afforded was poor and duration of immunity was short. These vaccines were replaced by live attenuated CPV vaccines, which provided excellent protection and longer duration of immunity. Currently the live attenuated vaccines are derived from either CPV2b isolates or the original type 2 virus. Since the type 2 virus has been entirely replaced in the field by 2a, 2b and now 2c viruses there has been concern over the level of protection afforded by attenuated type 2 vaccines (Pratelli et al., Clin. Diag. Lab. Immunol. 8, 612-615, 2001; Truyen, Vet. Microbiol. 69, 47-50, 1999).

However, based on studies with available monoclonal antibodies each new antigenic variant has lost at least one neutralising epitope compared with the former variant (Strassheim et al., Virology 198, 175-184, 1994; Pereira et al., supra). Previously it has been demonstrated that the live attenuated CPV2 vaccine is able to protect dogs against 2a and 2b field challenges (Greenwood et al., Vet. Record. 136, 63-67, 1995) even though cross-neutralisation studies conducted in vitro using sera raised against the various antigenic types do show marked differences (Pratelli et al., supra).

Recently, it was shown that live attenuated type 2 vaccine (Nobivac-Intervet) was able to protect dogs from challenge with the most recent CPV variant, CPV2c (Spibey et al., Vet. Microbiol 128, 48-55, 2008).

Nevertheless there exists a need in the field for vaccines that improve the immunity of animals, in particular cats, dogs and pigs against infection with new types of parvoviruses. However, such vaccines are not available, in particular, vaccines specific for Canine parvovirus type 2c are not available.

SUMMARY OF THE INVENTION

The present invention provides a solution to the above problem in that a vaccine is provided comprising a recombinant parvovirus comprising a DNA sequence obtainable from an attenuated first parvovirus wherein the DNA encoding the capsid protein or fragment thereof of said first parvovirus is replaced by a capsid protein or fragment thereof derivable from a second parvovirus, such as a canine parvovirus, more in particular a type 2c parvovirus and a pharmaceutically acceptable carrier.

Surprisingly it was found that such a vaccine was capable of inducing higher titers of protecting antibodies against a challenge with the second canine parvovirus while maintaining good immunity against type 2 strains whereas the recombinant canine parvovirus remained attenuated.

DETAILED DESCRIPTION OF THE INVENTION

Viral DNA encoding the capsid protein of a second canine parvovirus may be obtained from a strain isolated in the field by using ordinary skills of a person skilled in the art. In the examples section, such is illustrated by using a type 2c isolate. Viral DNA from an attenuated canine parvovirus is also available in the art, the examples show the isolation of an original type 2 virus contained in a vaccine strain obtained from Intervet (Nobivac parvo).

More in particular, viral DNA was obtained from a CPV type 2c field isolate. Each DNA preparation was digested with a different restriction enzyme such that such that two overlapping fragments were generated from each preparation. Fragments were purified and separated. Selected fragments were then transfected into susceptible cells. This is schematically shown in FIG. 1.

Upon natural recombination of the two fragments, a hybrid virus was obtained containing the capsid protein of a type 2c isolate in the context of the DNA sequence of a conventional attenuated type 2 virus. This virus was isolated, purified and admixed with a pharmaceutically acceptable carrier and used as a vaccine.

Dogs that received the new vaccine were challenged with field isolates of CPV type 2c virus and with the parental virus of the type 2 vaccine.

Surprisingly, the new vaccine provided an adequate antibody titer against conventional type 2 isolates and an improved protection against type 2c CPV.

Such a vaccine may advantageously be used in the protection of dogs against infection with canine parvovirus, in particular type 2c.

More in general, the above findings show that an attenuated virus may be used as the basis for a recombinant vaccine against infection with another canine parvovirus by exchanging the capsid region of the first canine parvovirus with the capsid region or the relevant fragments thereof of the second canine parvovirus.

Hence, the invention relates to a recombinant parvovirus comprising a DNA sequence obtainable from an attenuated first parvovirus wherein the DNA encoding the capsid protein or fragment thereof of said first parvovirus is replaced by a capsid protein or fragment thereof derivable from a second parvovirus.

The capsid proteins from the first and the second parvovirus need to be different in at least one amino acid. The term "capsid protein or fragment thereof" in this context means a full-length capsid protein or such a part thereof that comprises the difference in the capsid protein between the first and second parvovirus.

Preferably, the full-length capsid protein of the first parvovirus is replaced by the full-length capsid protein of the second parvovirus.

The terms "full-length" and "essentially full-length" as used herein, are meant to indicate that the protein or nucleic acid sequence contains all necessary elements to perform its function, preferably the sequence should contain all elements (amino acids or nucleotides) of the natural sequence.

The recombinant parvovirus according to the invention may be advantageously employed in a vaccine for the protection of animals against infection with parvovirus. Such vaccines were found to protect animals against infection with the first as well as the second virus whereas the recombinant vaccine remained attenuated such that it could not induce any clinical signs of parvovirus infection.

The invention also relates to a method for obtaining a recombinant parvovirus according to the invention comprising the steps of:
a. Obtaining at least one first DNA fragment from an attenuated first parvovirus strain, said first DNA fragment not encoding a capsid protein
b. Obtaining at least one second DNA fragment from a second parvovirus strain said second DNA fragment encoding a capsid protein
c. Transfecting a cell permissive for parvovirus with the DNA fragments obtained in steps a and b
d. Allowing the DNA fragments to recombine
e. Selecting an attenuated recombinant virus that encodes a viral capsid protein derived from the second parvovirus in the genetic context of the genome of the first parvovirus
f. Culturing the cell under conditions that allow the production of parvovirus in a cell culture
g. Obtaining the recombinant parvovirus from the cell culture Preferably, the parvovirus is a canine parvovirus, even more preferably, the first parvovirus is a type 2 canine parvovirus and the second canine parvovirus is a type 2c canine parvovirus; this results in a vaccine that protects dogs against infections with type 2 as well as type 2c while maintaining its attenuated properties.

In order to unequivocally show that an attenuation site does not reside in the capsid protein, the capsid protein gene in an attenuated strain was replaced by a chemically synthesised version, the sequence of which was derived from a virulent 2c field isolate. This method also yielded an attenuated virus according to the invention.

LEGENDS TO THE FIGURES

FIG. 1: Schematic representation of the natural recombination (non-GM) method of obtaining a hybrid 2/2c virus isolate. Two overlapping fragments from the type 2 vaccine and type 2c field virus were transfected into cells and virus isolated following homologous recombination.

Figure 2:
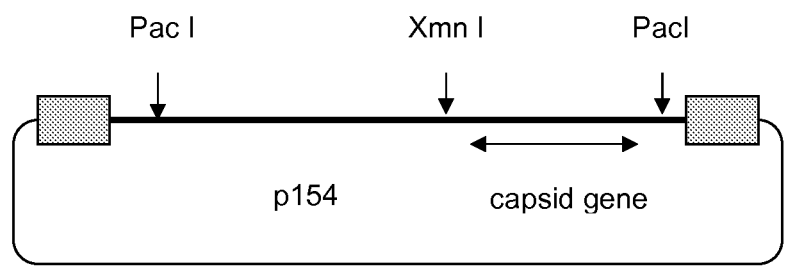

FIG. 2 Schematic representation of the infectious plasmid clone of CPV strain 154att showing the restriction enzyme sites Pac I and Xmn I. The shaded boxes illustrate the terminal palindrome sequences FIG. 3: Schematic showing the selected product of the partial Pac I/Xmn I digest that was selected for further manipulation FIG. 4: Plasmid containing the 154att vaccine virus DNA in which the capsid gene is substituted by a virulent CPV2c capsid sequence.

EXAMPLES

Example 1

Generation of Recombinant Virus

Strain 154 att was obtained from a commercially available Nobivac Parvo C (Intervet Schering-Plough Animal Health) and strain Jess was a field isolate of a type 2c virus.

Viruses were grown on adherent canine or feline kidney cells (eg A72 & CrFK) using M6B8 medium containing 5% foetal calf serum. Replicative form (RF) DNA was prepared from infected cell cultures using a modification of the standard "Hirt" method (McMaster et al 1981).

RF DNA prepared from the 154 att strain was digested with the restriction enzyme PstI and the fragments separated by agarose gel electrophoresis. The 3055 base pair (bp) band (corresponding to the left hand end of CPV) was excised from the gel and purified using Qiagen Qiaquick gel extraction columns. RF DNA isolated from CPV Jess infected cells was digested with the restriction enzyme Xmnl. Again the DNA fragments were separated by agarose gel electrophoresis followed by purification of an approximately 2750 by band (corresponding to the right hand end of CPV including the capsid sequence) using Qiagen Qiaquick gel extraction columns.

The purified 3055 by and 2750 bp fragments from 154att and Jess were combined and transfected into A72 or CrFK cells in culture. Transfections were performed using Lipofectamine 2000 (Invitrogen) with approximately 3 μg of each fragment, following the manufactures instructions.

Following transfection, cells were passaged and monitored by haemagglutination (HA) assay. Virus was detected by HA at pass 4. DNA sequence determination of hybrid viruses was performed using standard DNA sequencing protocols using either RF DNA or PCR fragment templates. Virus was purified by limiting dilution on adherent susceptible canine or feline cells.

Example 2

Recombinant Virus Constructed from Cloned Viral DNA

Recombinant virus was generated from cloned fragments. The genome of virus strain 154att was cloned into the standard cloning vector pBluescript (Stratagene inc.). In order to maintain the palindromic terminal sequences intact the plasmid was propagated in the bacterial host DL795 which is defective in a number of recombination systems. Cloning of parvovirus genomes has been described in the literature and the techniques required are known to someone skilled in the art.

The obtained clone of 154att (p154) was digested with the restriction enzyme Pac I such that the digestion was not allowed to go to completion, i.e. the restriction enzyme digest was only partial. The digested fragments were then subjected to digestion with the restriction enzyme Xmn I. The digested DNA fragments were then separated by agarose gel electrophoresis and the fragment indicated in the diagram below was excised from the gel and purified using Qiagen Qiaquick gel extraction columns. The Xmn I and right hand Pac sites flank the capsid region in the parvovirus genome.

The capsid gene of 154 att was replaced by the capsid gene of a virulent strain of CPV as follows. The Xmn I site and the right hand Pac I indicated in FIG. 2 lie outside the boundaries of the capsid gene. The approximately 110 bp sequence between the Pac I site and the end of the capsid gene differs significantly between the 154att strain and virulent isolates. There are as yet no recorded sequence changes in the short sequence (~55 bp) between the Xmn I site and the start of the capsid gene. Therefore in order to limit the exchange of material just to the capsid sequence; the virulent CPV capsid sequence was chemically synthesised and vaccine specific sequence between the PacI site and the capsid stop signal was retained. Below, the chemically synthesized sequence is shown containing the CPV capsid gene. The sequence as shown below is provided herein as SEQ ID NO: 1.

AGAGGCAGACCTGAGAGCCATCTTTACTTCTGAACAATTGGAAGAAGATTTTCGAGA

Xmn I

CGACTTGGATTAAGGTACGATGGCACCTCCGGCAAAGAGAGCCAGGAGAGGTAAGGGTGT

GTTAGTAAAGTGGGGGGAGAGGAAAGATTTAATAACTTAACTAAGTATGTCTTTTTTTAT

AGGACTTGTGCCTCCAGGTTATAAATATCTTGGGCCTGGGAACAGTCTTGACCAAGGAGA

ACCAACTAACCCTTCTGACGCCGCTGCAAAAGAACACGACGAAGCTTACGCTGCTTATCT

TCGCTCTGGTAAAAACCCATACTTATATTTCTCGCCAGCAGATCAACGCTTTATAGATCA

AACTAAGGACGCTAAAGATTGGGGGGGGAAAATAGGACATTATTTTTTTAGAGCTAAAAA

GGCAATTGCTCCAGTATTAACTGATACACCAGATCATCCATCAACATCAAGACCAACAAA

ACCAACTAAAAGAAGTAAACCACCACCTCATATTTTCATTAATCTTGCAAAAAAAAAAAA

AGCCGGTGCAGGACAAGTAAAAAGAGACAATCTTGCACCAATGAGTGATGGAGCAGTTCA

ACCAGACGGTGGTCAACCTGCTGTCAGAAATGAAAGAGCAACAGGATCTGGGAACGGGTC

TGGAGGCGGGGGTGGTGGTGGTTCTGGGGGTGTGGGGATTTCTACGGGTACTTTCAATAA

-continued

```
TCAGACGGAATTTAAATTTTTGGAAAACGGATGGGTGGAAATCACAGCAAACTCAAGCAG

ACTTGTACATTTAAATATGCCAGAAAGTGAAAATTATAGAAGAGTGGTTGTAAATAATTT

GGATAAAACTGCAGTTAACGGAAACATGGCTTTAGATGATACTCATGCACAAATTGTAAC

ACCTTGGTCATTGGTTGATGCAAATGCTTGGGGAGTTTGGTTTAATCCAGGAGATTGGCA

ACTAATTGTTAATACTATGAGTGAGTTGCATTTAGTTAGTTTTGAACAAGAAATTTTTAA

TGTTGTTTTAAAGACTGTTTCAGAATCTGCTACTCAGCCACCAACTAAAGTTTATAATAA

TGATTTAACTGCATCATTGATGGTTGCATTAGATAGTAATAATACTATGCCATTTACTCC

AGCAGCTATGAGATCTGAGACATTGGGTTTTTATCCATGGAAACCAACCATACCAACTCC

ATGGAGATATTATTTTCAATGGGATAGAACATTAATACCATCTCATACTGGAACTAGTGG

CACACCAACAAATATATACCATGGTACAGATCCAGATGATGTTCAATTTTATACTATTGA

AAATTCTGTGCCAGTACACTTACTAAGAACAGGTGATGAATTTGCTACAGGAACATTTTT

TTTTGATTGTAAACCATGTAGACTAACACATACATGGCAAACAAATAGAGCATTGGGCTT

ACCACCATTTCTAAATTCTTTGCCTCAAGCTGAAGGAGGTACTAACTTTGGTTATATAGG

AGTTCAACAAGATAAAAGACGTGGTGTAACTCAAATGGGAAATACAAACTATATTACTGA

AGCTACTATTATGAGACCAGCTGAGGTTGGTTATAGTGCACCATATTATTCTTTTGAGGC

GTCTACACAAGGGCCATTTAAAACACCTATTGCAGCAGGACGGGGGGAGCGCAAACAGA

TGAAAATCAAGCAGCAGATGGTGATCCAAGATATGCATTTGGTAGACAACATGGTCAAAA

AACTACCACAACAGGAGAAACACCTGAGAGATTTACATATATAGCACATCAAGATACAGG

AAGATATCCAGAAGGAGATTGGATTCAAAATATTAACTTTAACCTTCCTGTAACAGAAGA

TAATGTATTGCTACCAACAGATCCAATTGGAGGTAAAACAGGAATTAACTATACTAATAT

ATTTAATACTTATGGTCCTTTAACTGCATTAAATAATGTACCACCAGTTTATCCAAATGG

TCAAATTTGGGATAAAGAATTTGATACTGACTTAAAACCAAGACTTCATGTAAATGCACC

ATTTGTTTGTCAAAATAATTGTCCTGGTCAATTATTTGTAAAAGTTGCGCCTAATTTAAC

AAATGAATATGATCCTGATGCATCTGCTAATATGTCAAGAATTGTAACTTACTCAGATTT

TTGGTGGAAAGGTAAATTAGTATTTAAAGCTAAACTAAGAGCCTCTCATACTTGGAATCC

AATTCAACAAATGAGTATTAATGTAGATAACCAATTTAACTATGTACCAAGTAATATTGG

AGGTATGAAAATTGTATATGAAAAATCTCAGCTAGCACCTAGAAAATTATAT͟T͟A͟A͟CATAC

TTACTATGTTTTTATGTTTATTACATATCAACTAACACCTAGAAAATTATATTAATATAC

TTACTATGTTTTTATGTTTATTACATATTATTTTAAGATTAATTAAGGCGCGCC
                                                       PacI
```

The Xmn I & Pac I sites are indicated and underlined. The stop codon (TAA) of the capsid coding region The capsid (Vp1/Vp2) coding sequence is in bold.

Figure 3:
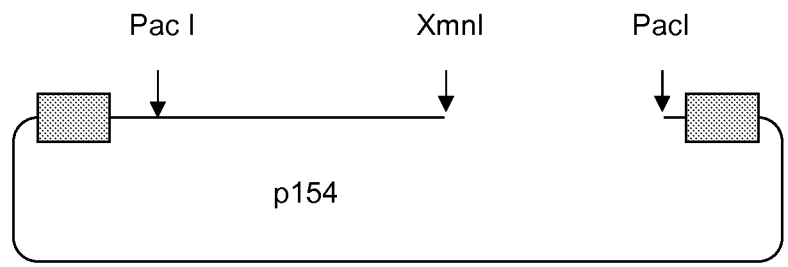
Figure 4:
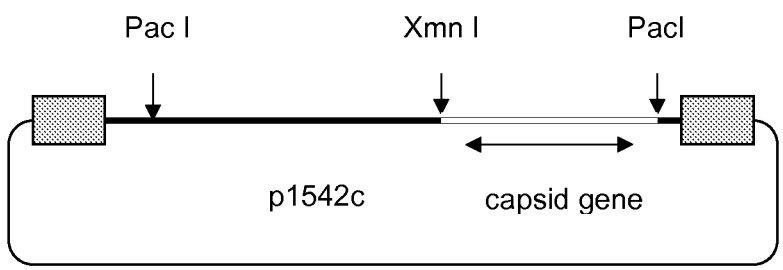

The synthesised fragment was liberated from the plasmid in which it was provided using the enzymes Xmn I and Pac I, it was then ligated to the fragment shown in FIG. 3. Competent *E.coli* (strain DL795) were transformed with the ligation mix using standard protocols and bacteria harbouring the recombinant plasmids isolated and identified. The resultant plasmid p1542c illustrated below (FIG. 4) was then prepared from the cloned *E.coli*.

Hybrid virus was prepared as follows. Plasmid p1542c DNA was transfected into A72 or CrFK cells in culture. Transfections were performed using Lipofectamine 2000 (Invitrogen) with approximately 3 microgram of DNA, following the manufacturer's instructions. Following transfection, cells were passaged and monitored by haemagglutination (HA) assay. Virus was detected by HA at pass 4. DNA sequence determination of hybrid viruses was performed using standard DNA sequencing protocols using either RF DNA or PCR fragment templates. Virus was purified by limiting dilution on adherent susceptible canine or feline cells.

Example 3

In Vivo Testing

Three groups of 6 week old SPF non-vaccinated pups born from non-vaccinated mothers, hence devoid of any maternally derived antibodies directed against CPV were inoculated with the 2/2c hybrid virus, and each of the parental viruses (type 2 vaccine and type 2c field virus). Animals were clinically monitored and blood samples taken.

Group 1 contained 5 dogs subcutaneously vaccinated with Parvo C, a conventional Intervet vaccine comprising a type 2 CPV. Group 2 contained 5 dogs subcutaneously vaccinated with the new hybrid 2/2c vaccine at 107.5 TCID50 per ml.

It was found that the dogs in group 1 exhibited a higher titer of specific antibodies against type 2 virus than against the hybrid. Group 2 dogs on the contrary, exhibited higher titers of hemagglutination inhibition (HAI) as well as Serum Neutralisation (SN) titers against the hybrid virus.

It may therefore be concluded that the hybrid virus strain provides improved protection against infection with CPV type 2c while maintaining adequate protection for conventional type 2 virus strains.

None of the dogs inoculated with the existing vaccine showed signs of disease, whereas control dogs which were inoculated with field virus exhibit severe haemorrhagic enteritis. Hence, we surprisingly found that the major attenuating mutations in CPV lie outside the capsid protein gene.

Example 4

Safety Testing

A study was performed to examine the safety of the 2/2c hybrid virus in puppies which had maternally derived antibody (MDA). All vaccinated puppies remained completely normal throughout the study. Moreover dogs which had been vaccinated with the hybrid virus developed a good serological response indicating that the hybrid virus was able to break through normal levels of MDA, an essential requirement of an effective canine parvovirus vaccine.

The invention claimed is:

1. An attenuated recombinant parvovirus comprising a DNA sequence obtained from an attenuated first parvovirus; wherein the DNA sequence encoding the capsid protein or fragment thereof of said first parvovirus is replaced by a DNA sequence encoding a capsid protein or fragment thereof derived from a second parvovirus; wherein said first parvovirus is a type 2 canine parvovirus; wherein said second parvovirus is a type 2c canine parvovirus; wherein the attenuated recombinant canine parvovirus comprises the DNA sequence encoding the capsid protein of a canine parvovirus type 2c isolate within the DNA sequence of an attenuated canine parvovirus type 2 virus; and wherein said fragment thereof of said second parvovirus comprises at least one amino acid difference from said fragment thereof of said first parvovirus.

2. The attenuated recombinant parvovirus according to claim 1 wherein the DNA sequence obtained from an attenuated first parvovirus is essentially full length.

3. The attenuated recombinant parvovirus according to claim 2, wherein said capsid protein from said second parvovirus is essentially full-length.

4. A vaccine for the protection of animals against infection with parvovirus, wherein said vaccine comprises the attenuated recombinant parvovirus according to claim 3 and a pharmaceutically acceptable carrier.

5. A method for obtaining a recombinant parvovirus according to claim 3, said method comprising the steps of:
    a. Obtaining at least one DNA fragment from an attenuated first parvovirus strain not encoding a capsid protein;
    b. Obtaining at least one DNA fragment from a second parvovirus strain encoding a capsid protein;
    c. Transfecting a cell permissive for parvovirus with the DNA fragments obtained in steps a and b;
    d. Allowing the DNA fragments to recombine;
    e. Selecting an attenuated recombinant virus that encodes a viral capsid protein derived from the second parvovirus in the genetic context of the genome of the first parvovirus;
    f Culturing the cell under conditions that allow the production of parvovirus in a cell culture; and
    g. Obtaining the recombinant parvovirus from the cell culture.

6. The attenuated recombinant parvovirus according to claim 1, wherein said capsid protein from said second parvovirus is essentially full-length.

7. A vaccine for the protection of animals against infection with parvovirus, wherein said vaccine comprises the attenuated recombinant parvovirus according to claim 6 and a pharmaceutically acceptable carrier.

8. A vaccine for the protection of animals against infection with parvovirus, wherein said vaccine comprises the attenuated recombinant parvovirus according to claim 2 and a pharmaceutically acceptable carrier.

9. A vaccine for the protection of animals against infection with parvovirus, wherein said vaccine comprises an attenuated recombinant parvovirus according to claim 1 and a pharmaceutically acceptable carrier.

10. A method for obtaining a recombinant parvovirus according to claim 6, said method comprising the steps of:
    a. Obtaining at least one DNA fragment from an attenuated first parvovirus strain not encoding a capsid protein;
    b. Obtaining at least one DNA fragment from a second parvovirus strain encoding a capsid protein;
    c. Transfecting a cell permissive for parvovirus with the DNA fragments obtained in steps a and b;
    d. Allowing the DNA fragments to recombine;
    e. Selecting an attenuated recombinant virus that encodes a viral capsid protein derived from the second parvovirus in the genetic context of the genome of the first parvovirus;

f Culturing the cell under conditions that allow the production of parvovirus in a cell culture; and
g. Obtaining the recombinant parvovirus from the cell culture.

11. A method for obtaining a recombinant parvovirus according to claim 2, said method comprising the steps of:
   a. Obtaining at least one DNA fragment from an attenuated first parvovirus strain not encoding a capsid protein;
   b. Obtaining at least one DNA fragment from a second parvovirus strain encoding a capsid protein;
   c. Transfecting a cell permissive for parvovirus with the DNA fragments obtained in steps a and b;
   d. Allowing the DNA fragments to recombine;
   e. Selecting an attenuated recombinant virus that encodes a viral capsid protein derived from the second parvovirus in the genetic context of the genome of the first parvovirus;
   f. Culturing the cell under conditions that allow the production of parvovirus in a cell culture; and
   g. Obtaining the recombinant parvovirus from the cell culture.

12. A method for obtaining a recombinant parvovirus according to claim 1, said method comprising the steps of:
   a. Obtaining at least one DNA fragment from an attenuated first parvovirus strain not encoding a capsid protein;
   b. Obtaining at least one DNA fragment from a second parvovirus strain encoding a capsid protein;
   c. Transfecting a cell permissive for parvovirus with the DNA fragments obtained in steps a and b;
   d. Allowing the DNA fragments to recombine;
   e. Selecting an attenuated recombinant virus that encodes a viral capsid protein derived from the second parvovirus in the genetic context of the genome of the first parvovirus;
   f. Culturing the cell under conditions that allow the production of parvovirus in a cell culture; and
   g. Obtaining the recombinant parvovirus from the cell culture.

13. A method of protecting an animal against infection with canine parvovirus comprising administering to the animal the vaccine of claim 9.

14. A method of protecting an animal against infection with canine parvovirus comprising administering to the animal the vaccine of claim 8.

15. A method of protecting an animal against infection with canine parvovirus comprising administering to the animal the vaccine of claim 7.

16. A method of protecting an animal against infection with canine parvovirus comprising administering to the animal the vaccine of claim 4.

* * * * *

SEQUENCE LISTING

```
<160> NUMBER OF SEQ ID NOS: 1

<210> SEQ ID NO 1
<211> LENGTH: 2451
<212> TYPE: DNA
<213> ORGANISM: canine parvovirus

<400> SEQUENCE: 1
agaggcagac ctgagagcca tctttacttc tgaacaattg gaagaagatt ttcgagacga      60
cttggattaa ggtacgatgg cacctccggc aaagagagcc aggagaggta agggtgtgtt     120
agtaaagtgg ggggagagga aagatttaat aacttaacta agtatgtgtt tttttatagg     180
acttgtgcct ccaggttata aatatcttgg gcctgggaac agtcttgacc aaggagaacc     240
aactaaccct tctgacgccg ctgcaaaaga acacgacgaa gcttacgctg cttatcttcg     300
ctctggtaaa aacccatact tatatttctc gccagcagat caacgcttta tagatcaaac     360
taaggacgct aaagattggg gggggaaaat aggacattat tttttttagag ctaaaaaggc     420 aattgctcca gtattaactg atacaccaga tcatccatca acatcaagac caacaaaacc     480
aactaaaaga agtaaaccac cacctcatat tttcattaat cttgcaaaaa aaaaaaaagc     540
cggtgcagga caagtaaaaa gagacaatct tgcaccaatg agtgatggag cagttcaacc     600
agacggtggt caacctgctg tcagaaatga aagagcaaca ggatctggga acgggtctgg     660 aggcggggt ggtggtggtt ctgggggtgt ggggatttct acgggtactt tcaataatca     720
gacggaattt aaatttttgg aaaacggatg ggtggaaatc acagcaaact caagcagact     780
tgtacattta aatatgccag aaagtgaaaa ttatagaaga gtggttgtaa ataatttgga     840
taaaactgca gttaacggaa acatggcttt agatgatact catgcacaaa ttgtaacacc     900
ttggtcattg gttgatgcaa atgcttgggg agtttggttt aatccaggag attggcaact     960
aattgttaat actatgagtg agttgcattt agttagtttt gaacaagaaa tttttaatgt    1020
tgttttaaag actgtttcag aatctgctac tcagccacca actaaagttt ataataatga    1080
tttaactgca tcattgatgg ttgcattaga tagtaataat actatgccat ttactccagc    1140
agctatgaga tctgagacat tgggttttta tccatggaaa ccaaccatac caactccatg    1200
gagatattat tttcaatggg atagaacatt aataccatct catactggaa ctagtggcac    1260
accaacaaat atataccatg gtacagatcc agatgatgtt caattttata ctattgaaaa    1320
ttctgtgcca gtacacttac taagaacagg tgatgaattt gctacaggaa cattttttttt    1380 tgattgtaaa ccatgtagac taacacatac atggcaaaca aatagagcat tgggcttacc    1440
```

-continued

```
accatttcta aattctttgc ctcaagctga aggaggtact aactttggtt atataggagt    1500
tcaacaagat aaaagacgtg gtgtaactca aatgggaaat acaaactata ttactgaagc    1560
tactattatg agaccagctg aggttggtta tagtgcacca tattattctt ttgaggcgtc    1620
tacacaaggg ccatttaaaa cacctattgc agcaggacgg gggggagcgc aaacagatga    1680
aaatcaagca gcagatggtg atccaagata tgcatttggt agacaacatg gtcaaaaaac    1740
taccacaaca ggagaaacac ctgagagatt tacatatata gcacatcaag atacaggaag    1800
atatccagaa ggagattgga ttcaaaatat taactttaac cttcctgtaa cagaagataa    1860
tgtattgcta ccaacagatc caattggagg taaaacagga attaactata ctaatatatt    1920
taatacttat ggtcctttaa ctgcattaaa taatgtacca ccagtttatc caaatggtca    1980
aatttgggat aaagaatttg atactgactt aaaaccaaga cttcatgtaa atgcaccatt    2040
tgtttgtcaa aataattgtc ctggtcaatt atttgtaaaa gttgcgccta atttaacaaa    2100
tgaatatgat cctgatgcat ctgctaatat gtcaagaatt gtaacttact cagattttg     2160 gtggaaaggt aaattagtat ttaaagctaa actaagagcc tctcatactt ggaatccaat    2220
tcaacaaatg agtattaatg tagataacca atttaactat gtaccaagta atattggagg    2280
tatgaaaatt gtatatgaaa aatctcagct agcacctaga aaattatatt aacatactta    2340
ctatgttttt atgtttatta catatcaact aacacctaga aaattatatt aatatactta    2400
ctatgttttt atgtttatta catattattt taagattaat taaggcgcgc c             2451
```